United States Patent [19]
Corbett

[11] Patent Number: 4,513,010

[45] Date of Patent: Apr. 23, 1985

[54] METHOD OF TREATING NAVICULAR DISEASE IN HORSES

[75] Inventor: Lorimer J. Corbett, Sydney, Australia

[73] Assignee: Medical Research (Marketing) Pty, Ltd., North Ryde, Australia

[21] Appl. No.: 495,111

[22] Filed: May 16, 1983

[30] Foreign Application Priority Data

Jun. 18, 1982 [AU] Australia ............................... PF4493

[51] Int. Cl.$^3$ ......................................... A61K 31/135
[52] U.S. Cl. .................................................. 514/651
[58] Field of Search ........................................ 424/330

[56] References Cited

PUBLICATIONS

Lambert et al.—Chem. Abst., vol. 69, (1967), p. 80898v.

Primary Examiner—Sam Rosen

[57] ABSTRACT

A method of treating navicular disease in horses comprising the administration of Isoxsuprine over an extended period and an injectable paste composition including isoxsuprine hydrochloride and pharmaceutically acceptable carriers and flavorants for use in said method.

11 Claims, No Drawings

METHOD OF TREATING NAVICULAR DISEASE IN HORSES

FIELD OF THE INVENTION

This invention relates to the treatment of navicular disease in horses.

BACKGROUND OF THE INVENTION

Navicular disease in a progressive and hitherto irreversible lameness affecting either or both of the forelimbs of a horse and is characterised by an increasingly stumbling gait. Hitherto, the disease has invariably rendered the horse unfit for work.

Navicular disease is essentially an ischaemic necrosis of the navicular bone within the hoof of the horse. It has been recognized since the latter part of the 19th century and was widely thought to have been an arthritic type pathogenesis. However, more recently it has been suggested that the necrosis of the navicular bone is due to a poor blood supply to the bone arising from thrombosis of branches of the navicular artery.

The present invention arose from experimental attempts to increase the supply of blood to the navicular bone by the use of vasodilating agents.

Isoxsuprine hydrochloride is a known chemical of molecular formula $C_{18}H_{23}NO_3HCl$, more fully termed 1-p-hydroxyphenol-2-(1-methyl-2-phenoxyethylamino)propan-1-Ol-hydrochloride and has the structural formula

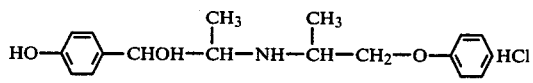

In veterinary practice Isoxsuprine hydrochloride has been utilised hitherto as an intramuscular injectant to bring about muscle relaxation, especially relaxation of the muscles of the uterus in animals undergoing Caeserean section, embryotomy, and in cases of uterine torsion and incomplete cervical dilation. However, it was known to have a peripheral vasodilatory effect in man and therefore in the aforesaid experimental work was considered as a possible agent for increasing the blood supply to the navicular bone in horses.

SUMMARY OF THE INVENTION

According to the invention navicular disease in horses is treated by the administration of Isoxsuprine or a pharmaceutically acceptable compound thereof over an extended period.

DETAILED DESCRIPTION

According to preferred embodiments of the invention the Isoxsuprine hydrochloride is included as the active ingredient in a pharmaceutically acceptable paste which may be administered orally to the horse shortly prior to, say thirty minutes before, feeding, twice daily.

The preferred dosage rate at each administration comprises 0.6 mg of active ingredient per Kg bodyweight and may be administered at that level for 21 days followed by the same dosage once daily progressing to once every other day over a period of a further 21 days. Thus, it will be seen that according to the invention high levels of Isoxsuprine hydrochloride are administered over a substantial period.

As is customary, paste medicaments may be administered by means of a syringe inserted into the side of a horse's empty mouth for deposition of the paste on the back of the tongue. Once the syringe is withdrawn the horse's mouth should be held closed for a few seconds to ensure that the full dose is swallowed.

It is thought that treatment according to the invention should not be given to pregnant mares, post partum or following recent arterial haemorrhage.

A typical paste formulation for use in treatments according to the invention may comprise the following ingredients in the parts by weight indicated:

| | |
|---|---|
| ISOXSUPRINE HYDROCHLORIDE | 40.0 |
| PARAFFIN OIL | 610.5 |
| POLYSORBATE 80 | 8.0 |
| PROPYL PARABEN | 0.2 |
| METHYL PARABEN | 0.8 |
| SODIUM CYCLAMATE | 2.0 |
| PRECIPITATED SILICONE DIOXIDE | 163.0 |
| ANISEED FLAVOUR | 1.5 |
| ORANGE COLOUR (C.I.15985) | 0.1 |
| WATER | 142.5 |

As an alternative mode of treatment the Isoxsuprine hydrochloride may be incorporated in a powdered formulation for admixture with a dry feed and a typical formulation of that kind may comprise the following ingredients in the parts by weight indicated:

| | |
|---|---|
| ISOXSUPRINE HYDROCHLORIDE | 100 |
| CORN FLOUR | 636 |
| LACTOSE | 224 |
| TALCUM POWDER | 40 |

It will be appreciated that the above-mentioned dosage rates and times are by way of example only and would be adjusted by a veterinarian in individual cases depending upon the clinical progress of the horse being treated.

As a further guide to the results which may be anticipated when treating horses for navicular disease in accordance with the invention the following case history of the experimental treatment of a group of 16 horses is presented.

All of the horses were diagnosed as having navicular disease by a set routine of diagnostic tests and radiographic procedures. In particular, the horses were all initially lame in one or both front legs and as is typical in navicular disease the lameness was increased following backward flexion of the fetlock and phalangeal joints for one minute. The lameness was abolished by blocking the branches of the palmar digital nerves to the navicular bone and bursa with local anesthetic and radiographs taken in the upright pedal position showed the normally triangular vascular channels to be rounded to an inverted flask shape.

As a result of the foregoing diagnostic tests 16 of the initially lame horses were diagnosed as having navicular disease and were commenced on daily treatment with the above-mentioned paste composition at a dosage rate of 0.6 mg/Kg (Isoxsuprine hydrochloride/bodyweight) given twice daily. The dosage rate was arrived at by clinical assessment by increasing the dosage until horses showed a positive clinical response.

Each horse was dosed about twenty to thirty minutes prior to feeding.

The initial treatment period was 21 days. However, in some horses extensions of treatment, normally in increments of 21 days was found to be necessary.

In horses that responded well to the initial therapy, the treatment was discontinued at the end of the appropriate course. However, in five of the horses remission of clinical signs was delayed although improvement was noted early in the treatment.

The treatment was discontinued on a programmed withdrawal dosage of 0.6 mg/Kg, once daily for 10-14 days, then 0.3 mg/Kg, once daily for 7-10 days. The set withdrawal programme was instigated after four horses appeared to suffer a relapse when treatment was discontinued suddenly when supply of the paste ran out. Programmed withdrawal alleviated this phenomenon.

The response to the treatment was a complete success in eleven out of the sixteen cases (68.75%).

In the five cases where complete remission of clinical signs did not take place, navicular disease was found to be not the sole contributing cause of lameness. Two of the remaining five horses did not exhibit relief of lameness following palmar digital nerve block, although changes consistent with navicular disease were evidenced by radiographs. These horses showed reduction in lameness but did not become completely sound after the nerve block failed to exhibit a positive reaction. This probably indicates that other underlying lameness problems existed in conjunction with navicular disease.

It will be understood that treatment according to the invention may be administered orally in forms other than as a paste, or powder, or granules and it is believed may in suitable forms be administered by injection or topically.

While the invention has been herein described primarily with reference to isoxsuprine hydrochloride those skilled in the art will recognize from the disclosure hereof that close substitutes for example isoxsuprine lactate, isoxuprine resinate, and other closely related isoxsuprine compounds which have similar pharmacological properties to isoxsuprine hydrochloride, could be expected to provide similar benefit. Accordingly the invention extends to include such substitutes.

I claim:

1. A method of treating navicular disease in horses comprising the administration of an effective amount of Isoxsuprine over an extended period.

2. A method according to claim 1 wherein the effective amount is about 0.3 mg per kg administered once daily.

3. A method of treating navicular disease in horses comprising the administration of an effective amount of a pharmaceutically acceptable compound of isoxsuprine over an extended period.

4. A method according to claim 3 wherein said compound is isoxsuprine hydrochloride.

5. A method according to claim 3 wherein the compound is administered orally.

6. A method according to claim 3 wherein the compound is administered orally twice daily for at least twenty-one days.

7. A method according to claim 5 wherein the administration is continued at a lesser daily dosage for a further period following said at least twenty-one days.

8. A method according to claim 5 wherein the administration is by way of an orally injectable paste containing the isoxsuprine compound.

9. A method according to claim 8 wherein said paste comprises:
ISOXSUPRINE HYDROCHLORIDE
PARAFFIN OIL
POLYSORBATE 80
PROPYL PARABEN
METHYL PARABEN
PRECIPITATED SILICONE DIOXIDE
FLAVOURING AGENT
WATER.

10. A method according to claim 5 wherein the administration is by way of an edible powder containing the isoxsuprine compound.

11. A method according to claim 10 wherein said powder comprises:
ISOXSUPRINE HYDROCHLORIDE
CEREAL FLOUR
LACTOSE
TALCUM POWDER.

* * * * *